US008827135B2

(12) United States Patent
Amid et al.

(10) Patent No.: US 8,827,135 B2
(45) Date of Patent: Sep. 9, 2014

(54) HERNIA STAPLER WITH INTEGRATED MESH MANIPULATOR

(75) Inventors: Parviz K. Amid, Calabasas, CA (US); Christian Martin, Miami, FL (US); Scott Arp, Village of Palmetto Bay, CA (US)

(73) Assignee: TransEnterix, Inc., Morrisville, NC (US)

( * ) Notice: Subject to any disclaimer, the term of this patent is extended or adjusted under 35 U.S.C. 154(b) by 0 days.

(21) Appl. No.: 12/880,492

(22) Filed: Sep. 13, 2010

(65) Prior Publication Data

US 2010/0327042 A1    Dec. 30, 2010

Related U.S. Application Data

(63) Continuation of application No. PCT/US2009/037119, filed on Mar. 13, 2009.

(60) Provisional application No. 61/036,644, filed on Mar. 14, 2008.

(51) Int. Cl.
*A61B 17/04* (2006.01)
*A61B 17/10* (2006.01)
*A61B 17/068* (2006.01)
*A61B 17/00* (2006.01)
*A61F 2/00* (2006.01)
*A61B 17/064* (2006.01)

(52) U.S. Cl.
CPC ... *A61B 17/0684* (2013.01); *A61B 2017/00349* (2013.01); *A61B 17/00234* (2013.01); *A61F 2/0063* (2013.01); *A61B 17/0644* (2013.01)
USPC ..................................... 227/176.1

(58) Field of Classification Search
USPC ............. 227/175.1–182.1; 606/139, 142, 143
See application file for complete search history.

(56) References Cited

U.S. PATENT DOCUMENTS

| 3,777,538 A | 12/1973 | Weatherly et al. |
| 3,837,555 A | 9/1974 | Green |

(Continued)

FOREIGN PATENT DOCUMENTS

| WO | WO 02/19920 A1 | 3/2002 |
| WO | WO 2004096057 A2 * | 11/2004 |
| WO | WO 2007/030676 A2 | 3/2007 |

OTHER PUBLICATIONS

Chapter 14, "Lichtenstein Tension-Free Hernioplasty for the Repair of Primary and Recurrent Inguinal Hernias", Parviz K. Amid, pp. 149-157, of Nyhus and Condon's Hernia, Fifth Edition, edited by Robert J. Fitzgibbons and A. Gerson Greenburg, published by Lippincott Williams & Wilkins, Philadelphia, 2002.

(Continued)

*Primary Examiner* — Robert Long
(74) *Attorney, Agent, or Firm* — Woodard, Emhardt, Moriarty, McNett & Henry LLP

(57) ABSTRACT

A surgical stapler for use during an open hernia repair comprises an elongated shaft having a handle 120 at its proximal end and a downwardly disposed staple discharge head 130 at its distal end. A squeeze trigger 122 on the handle 120 is operable to cause a supply of staples 160 to be selectively discharged from the port. One or more mesh manipulators 150 are provided on the head 130 and serve to assist in positioning or otherwise manipulating surgical mesh prior to fixation with the staples.

18 Claims, 11 Drawing Sheets

(56) References Cited

U.S. PATENT DOCUMENTS

| | | | |
|---|---|---|---|
| 4,014,492 A | 3/1977 | Rothfuss | |
| 4,242,902 A * | 1/1981 | Green | 72/409.01 |
| 4,317,451 A | 3/1982 | Cerwin et al. | |
| 4,428,376 A | 1/1984 | Mericle | |
| 4,485,816 A | 12/1984 | Krumme | |
| 4,500,025 A * | 2/1985 | Skwor | 227/19 |
| 4,506,669 A * | 3/1985 | Blake, III | 606/150 |
| 4,523,707 A | 6/1985 | Blake et al. | |
| 4,526,174 A | 7/1985 | Froehlich | |
| 4,527,726 A * | 7/1985 | Assell et al. | 227/19 |
| 4,540,110 A * | 9/1985 | Bent et al. | 227/8 |
| 4,548,202 A | 10/1985 | Duncan | |
| 4,627,437 A | 12/1986 | Bedi et al. | |
| 4,648,541 A * | 3/1987 | Mongeon | 227/19 |
| 4,669,647 A * | 6/1987 | Storace | 227/19 |
| 4,719,917 A | 1/1988 | Barrows et al. | |
| 4,773,420 A * | 9/1988 | Green | 227/178.1 |
| 5,015,249 A | 5/1991 | Nakao et al. | |
| 5,084,057 A | 1/1992 | Green et al. | |
| 5,104,394 A * | 4/1992 | Knoepfler | 606/143 |
| 5,158,567 A | 10/1992 | Green | |
| 5,161,725 A | 11/1992 | Murray et al. | |
| 5,174,487 A | 12/1992 | Rothfuss | |
| 5,217,472 A | 6/1993 | Green et al. | |
| 5,220,928 A | 6/1993 | Oddsen et al. | |
| 5,240,164 A | 8/1993 | Murray et al. | |
| 5,246,156 A | 9/1993 | Rothfuss et al. | |
| 5,254,126 A * | 10/1993 | Filipi et al. | 606/146 |
| 5,257,713 A | 11/1993 | Green et al. | |
| 5,281,236 A * | 1/1994 | Bagnato et al. | 606/139 |
| 5,289,963 A * | 3/1994 | McGarry et al. | 227/175.1 |
| 5,290,217 A | 3/1994 | Campos | |
| 5,297,714 A | 3/1994 | Kramer | |
| 5,304,204 A | 4/1994 | Bregen | |
| 5,333,772 A | 8/1994 | Rothfuss et al. | |
| 5,350,400 A | 9/1994 | Esposito et al. | |
| 5,354,312 A | 10/1994 | Brinkerhoff et al. | |
| 5,356,064 A * | 10/1994 | Green et al. | 227/177.1 |
| 5,364,002 A * | 11/1994 | Green et al. | 227/177.1 |
| 5,366,479 A * | 11/1994 | McGarry et al. | 606/219 |
| 5,376,097 A | 12/1994 | Phillips | |
| 5,381,943 A | 1/1995 | Allen et al. | |
| 5,389,102 A | 2/1995 | Green et al. | |
| 5,403,326 A * | 4/1995 | Harrison et al. | 606/139 |
| 5,413,272 A | 5/1995 | Green et al. | |
| 5,423,856 A | 6/1995 | Green | |
| 5,456,400 A | 10/1995 | Shichman et al. | |
| 5,470,010 A | 11/1995 | Rothfuss et al. | |
| 5,484,095 A | 1/1996 | Green et al. | |
| 5,497,933 A * | 3/1996 | DeFonzo et al. | 227/175.1 |
| 5,501,654 A * | 3/1996 | Failla et al. | 600/204 |
| 5,507,754 A * | 4/1996 | Green et al. | 606/139 |
| 5,527,318 A | 6/1996 | McGarry | |
| 5,536,251 A * | 7/1996 | Evard et al. | 604/93.01 |
| 5,540,716 A | 7/1996 | Hlavacek | |
| 5,549,637 A * | 8/1996 | Crainich | 606/207 |
| 5,560,532 A | 10/1996 | DeFonzo et al. | |
| 5,562,682 A | 10/1996 | Oberlin et al. | |
| 5,564,615 A | 10/1996 | Bishop et al. | |
| 5,573,541 A * | 11/1996 | Green et al. | 606/143 |
| 5,575,799 A | 11/1996 | Bolanos et al. | |
| 5,577,654 A | 11/1996 | Bishop | |
| 5,588,580 A | 12/1996 | Paul et al. | |
| 5,588,581 A | 12/1996 | Conlon et al. | |
| 5,601,224 A | 2/1997 | Bishop et al. | |
| 5,607,095 A | 3/1997 | Smith et al. | |
| 5,618,311 A | 4/1997 | Gryskiewicz | |
| 5,626,587 A | 5/1997 | Bishop et al. | |
| 5,630,540 A | 5/1997 | Blewett | |
| 5,634,584 A | 6/1997 | Okorocha et al. | |
| 5,662,662 A | 9/1997 | Bishop et al. | |
| 5,669,918 A | 9/1997 | Balazs et al. | |
| 5,725,554 A | 3/1998 | Simon et al. | |
| 5,743,456 A | 4/1998 | Jones et al. | |
| 5,766,187 A * | 6/1998 | Sugarbaker | 606/148 |
| 5,797,536 A | 8/1998 | Smith et al. | |
| 5,810,846 A * | 9/1998 | Virnich et al. | 606/142 |
| 5,810,882 A | 9/1998 | Bolduc et al. | |
| 5,817,109 A | 10/1998 | McGarry et al. | |
| 5,829,662 A * | 11/1998 | Allen et al. | 227/177.1 |
| 5,893,855 A * | 4/1999 | Jacobs | 606/150 |
| 5,908,149 A | 6/1999 | Welch et al. | |
| 5,937,951 A | 8/1999 | Izuchukwu et al. | |
| 5,938,101 A | 8/1999 | Izuchukwu et al. | |
| 6,129,740 A | 10/2000 | Michelson | |
| 6,273,903 B1 | 8/2001 | Wilk | |
| 6,302,311 B1 * | 10/2001 | Adams et al. | 227/176.1 |
| 6,318,616 B1 | 11/2001 | Pasqualucci et al. | |
| 6,450,391 B1 * | 9/2002 | Kayan et al. | 227/176.1 |
| 6,511,489 B2 | 1/2003 | Field et al. | |
| 6,533,762 B2 * | 3/2003 | Kanner et al. | 604/175 |
| 6,544,271 B1 * | 4/2003 | Adams et al. | 606/139 |
| 6,582,452 B2 * | 6/2003 | Coleman et al. | 606/213 |
| 6,601,748 B1 | 8/2003 | Fung et al. | |
| 6,609,322 B1 | 8/2003 | Michelson | |
| 6,616,686 B2 * | 9/2003 | Coleman et al. | 606/219 |
| 6,638,297 B1 | 10/2003 | Huitema | |
| 6,652,538 B2 | 11/2003 | Kayan et al. | |
| 6,669,073 B2 | 12/2003 | Milliman et al. | |
| 6,669,714 B2 * | 12/2003 | Coleman et al. | 606/219 |
| 6,679,904 B2 * | 1/2004 | Gleeson et al. | 606/219 |
| 6,685,712 B2 * | 2/2004 | Cummins et al. | 606/139 |
| 6,786,382 B1 | 9/2004 | Hoffman | |
| 6,926,731 B2 * | 8/2005 | Coleman et al. | 606/213 |
| 6,953,139 B2 | 10/2005 | Milliman et al. | |
| 7,004,950 B1 | 2/2006 | Collins et al. | |
| 7,008,435 B2 * | 3/2006 | Cummins | 606/139 |
| 7,014,638 B2 | 3/2006 | Michelson | |
| 7,048,171 B2 | 5/2006 | Thornton et al. | |
| 7,056,330 B2 | 6/2006 | Gayton | |
| 7,059,331 B2 * | 6/2006 | Adams et al. | 128/898 |
| 7,090,684 B2 * | 8/2006 | McGuckin et al. | 606/139 |
| 7,163,551 B2 * | 1/2007 | Anthony et al. | 606/219 |
| 7,213,736 B2 | 5/2007 | Wales et al. | |
| 7,220,237 B2 | 5/2007 | Gannoe et al. | |
| 7,225,964 B2 | 6/2007 | Mastri et al. | |
| 7,229,428 B2 | 6/2007 | Gannoe et al. | |
| RE39,841 E | 9/2007 | Bilotti et al. | |
| 7,320,692 B1 * | 1/2008 | Bender et al. | 606/139 |
| 7,401,720 B1 | 7/2008 | Durrani | |
| 7,422,138 B2 | 9/2008 | Bilotti et al. | |
| 7,434,716 B2 | 10/2008 | Viola | |
| 7,452,368 B2 | 11/2008 | Liberatore et al. | |
| 7,464,847 B2 | 12/2008 | Viola et al. | |
| 7,473,258 B2 | 1/2009 | Clauson et al. | |
| 7,510,106 B2 * | 3/2009 | Manabe | 227/107 |
| 7,530,484 B1 | 5/2009 | Durrani | |
| 7,530,984 B2 * | 5/2009 | Sonnenschein et al. | 606/139 |
| 7,533,790 B1 | 5/2009 | Knodel et al. | |
| 7,552,853 B2 * | 6/2009 | Mas et al. | 227/175.1 |
| 7,556,185 B2 | 7/2009 | Viola | |
| 7,556,186 B2 | 7/2009 | Milliman | |
| 7,615,058 B2 * | 11/2009 | Sixto et al. | 606/142 |
| 7,621,925 B2 * | 11/2009 | Saadat et al. | 606/139 |
| 7,624,903 B2 * | 12/2009 | Green et al. | 227/179.1 |
| 7,637,905 B2 * | 12/2009 | Saadat et al. | 606/1 |
| 7,651,017 B2 | 1/2010 | Ortiz et al. | |
| 7,708,181 B2 * | 5/2010 | Cole et al. | 227/176.1 |
| 7,736,374 B2 * | 6/2010 | Vaughan et al. | 606/153 |
| 7,744,613 B2 * | 6/2010 | Ewers et al. | 606/153 |
| 7,766,208 B2 | 8/2010 | Epperly et al. | |
| 7,771,440 B2 * | 8/2010 | Ortiz et al. | 606/142 |
| 7,776,057 B2 * | 8/2010 | Laufer et al. | 606/139 |
| 7,794,474 B2 * | 9/2010 | Michler et al. | 606/219 |
| 7,857,187 B2 | 12/2010 | Milliman | |
| 7,866,526 B2 * | 1/2011 | Green et al. | 227/175.1 |
| 7,914,543 B2 * | 3/2011 | Roth et al. | 606/153 |
| 7,942,884 B2 * | 5/2011 | Vahid et al. | 606/139 |
| 7,954,688 B2 * | 6/2011 | Argentine et al. | 227/176.1 |
| 7,997,468 B2 * | 8/2011 | Farascioni | 227/176.1 |
| 8,011,553 B2 | 9/2011 | Mastri et al. | |
| 8,011,555 B2 | 9/2011 | Tarinelli et al. | |
| 8,056,788 B2 | 11/2011 | Mastri et al. | |
| 8,066,720 B2 | 11/2011 | Knodel et al. | |

(56) References Cited

U.S. PATENT DOCUMENTS

| | | | |
|---|---|---|---|
| 8,123,101 B2 | 2/2012 | Racenet et al. | |
| 8,136,711 B2 * | 3/2012 | Beardsley et al. | 227/175.1 |
| 8,186,556 B2 | 5/2012 | Viola | |
| 8,231,041 B2 | 7/2012 | Marczyk et al. | |
| 8,252,009 B2 * | 8/2012 | Weller et al. | 606/151 |
| 8,393,516 B2 * | 3/2013 | Kostrzewski | 227/180.1 |
| 8,469,972 B2 * | 6/2013 | Harris et al. | 606/139 |
| 8,500,777 B2 * | 8/2013 | Harris et al. | 606/216 |
| 2002/0049472 A1 | 4/2002 | Coleman et al. | |
| 2002/0065535 A1 | 5/2002 | Kneifel et al. | |
| 2002/0077660 A1 | 6/2002 | Kayan et al. | |
| 2002/0117534 A1 * | 8/2002 | Green et al. | 227/176.1 |
| 2003/0120289 A1 | 6/2003 | McGuckin et al. | |
| 2003/0199924 A1 * | 10/2003 | Coleman et al. | 606/213 |
| 2003/0222118 A1 | 12/2003 | Brown | |
| 2004/0006372 A1 | 1/2004 | Racenet et al. | |
| 2004/0044364 A1 | 3/2004 | DeVries et al. | |
| 2004/0073237 A1 | 4/2004 | Leinsing | |
| 2004/0073257 A1 | 4/2004 | Spitz | |
| 2004/0138525 A1 * | 7/2004 | Saadat et al. | 600/104 |
| 2004/0138682 A1 | 7/2004 | Onuki et al. | |
| 2004/0138705 A1 | 7/2004 | Heino et al. | |
| 2004/0173659 A1 * | 9/2004 | Green et al. | 227/176.1 |
| 2004/0230208 A1 | 11/2004 | Shayani | |
| 2004/0243151 A1 * | 12/2004 | Demmy et al. | 606/139 |
| 2004/0267310 A1 | 12/2004 | Racenet et al. | |
| 2005/0051597 A1 * | 3/2005 | Toledano | 227/176.1 |
| 2005/0080434 A1 * | 4/2005 | Chung et al. | 606/148 |
| 2005/0159777 A1 | 7/2005 | Spitz | |
| 2005/0216057 A1 * | 9/2005 | Coleman et al. | 606/219 |
| 2005/0256537 A1 | 11/2005 | Cummins et al. | |
| 2005/0267530 A1 | 12/2005 | Cummins | |
| 2006/0097026 A1 | 5/2006 | Shelton, IV | |
| 2007/0043384 A1 * | 2/2007 | Ortiz et al. | 606/142 |
| 2007/0080188 A1 * | 4/2007 | Spence et al. | 227/175.1 |
| 2007/0114261 A1 | 5/2007 | Ortiz et al. | |
| 2007/0213585 A1 * | 9/2007 | Monassevitch et al. | 600/104 |
| 2007/0282356 A1 * | 12/2007 | Sonnenschein et al. | 606/153 |
| 2008/0000941 A1 | 1/2008 | Sonnenschein et al. | |
| 2008/0065153 A1 | 3/2008 | Allard et al. | |
| 2008/0065154 A1 | 3/2008 | Allard et al. | |
| 2008/0135600 A1 | 6/2008 | Hiranuma et al. | |
| 2008/0173691 A1 * | 7/2008 | Mas et al. | 227/175.1 |
| 2008/0217376 A1 | 9/2008 | Clauson et al. | |
| 2008/0243143 A1 | 10/2008 | Kuhns et al. | |
| 2008/0249565 A1 * | 10/2008 | Michler et al. | 606/219 |
| 2008/0269801 A1 * | 10/2008 | Coleman et al. | 606/213 |
| 2008/0272173 A1 | 11/2008 | Coleman et al. | |
| 2009/0069806 A1 * | 3/2009 | De La Mora Levy et al. | 606/46 |
| 2009/0105535 A1 * | 4/2009 | Green et al. | 600/106 |
| 2009/0134198 A1 | 5/2009 | Knodel et al. | |
| 2009/0242609 A1 | 10/2009 | Kanner | |
| 2009/0277949 A1 * | 11/2009 | Viola et al. | 227/178.1 |
| 2009/0308908 A1 * | 12/2009 | Green et al. | 227/176.1 |
| 2009/0314820 A1 * | 12/2009 | Green et al. | 227/176.1 |
| 2009/0318936 A1 * | 12/2009 | Harris et al. | 606/139 |
| 2010/0012704 A1 | 1/2010 | Racenet et al. | |
| 2010/0094315 A1 * | 4/2010 | Beardsley et al. | 606/143 |
| 2010/0320252 A1 | 12/2010 | Viola et al. | |
| 2010/0327042 A1 * | 12/2010 | Amid et al. | 227/176.1 |
| 2011/0049213 A1 * | 3/2011 | Schneider et al. | 227/120 |
| 2011/0168756 A1 | 7/2011 | Racenet et al. | |
| 2011/0168758 A1 | 7/2011 | Mastri et al. | |
| 2011/0218550 A1 | 9/2011 | Ma | |
| 2011/0297730 A1 | 12/2011 | Mastri et al. | |
| 2011/0315704 A1 | 12/2011 | Stopek | |
| 2012/0104073 A1 | 5/2012 | Milliman et al. | |
| 2012/0160893 A1 * | 6/2012 | Harris et al. | 227/175.1 |
| 2012/0193391 A1 * | 8/2012 | Michler et al. | 227/175.1 |
| 2012/0234898 A1 | 9/2012 | Shelton et al. | |
| 2013/0306704 A1 * | 11/2013 | Balbierz et al. | 227/176.1 |

OTHER PUBLICATIONS

Chapter 23, "The Transabdominal Preperitoneal Laparoscopic Herniorrhaphy", Fitzgibbons & Filipi, pp. 256-268 of Nyhus and Condon's Hernia, Fifth Edition, edited by Robert J. Fitzgibbons and A. Gerson Greenburg, published by Lippincott Williams & Wilkins, Philadelphia, 2002.
Search Report from parent PCT/US2009/037119.
Written Opinion from parent PCT/US2009/037119.
China Application No. 200980108633.1 English Translation of Office Action mailed Feb. 13, 2012.
International Patent Application No. PCT/US2009/037119 International Preliminary Report on Patentability mailed Sep. 23, 2010.
International Patent Application No. PCT/US2009/037119 Search Report mailed Oct. 28, 2009.
Japan Application No. 2010-550893, English Translation of Notice of Reasons for Rejection mailed Jun. 11, 2013.
Singapore Application No. 201006248-7 Written Opinion mailed Sep. 9, 2011.
U.S Appl. No. 13/425,590 to Amid et al., Final Office Action mailed Jun. 3, 2013.
U.S. Appl. No. 13/425,590 to Amid et al., Office Action mailed Oct. 10, 2013.
U.S. Appl. No. 13/425,590 to Amid et al., Final Office Action mailed Mar. 27, 2014.
European Application 09720716 Extended Search Report mailed Feb. 26, 2014.

* cited by examiner

HERNIA STAPLER WITH INTEGRATED MESH MANIPULATOR

RELATED APPLICATION DATA

This application is a continuation of PCT/US2009/037119 filed Mar. 13, 2009, which claims the benefit of U.S. Provisional Application Ser. No. 61/036,644 filed Mar. 14, 2008, the disclosure of which are hereby incorporated by reference.

BACKGROUND

This application is generally related to means for applying surgical staples to fasten a surgical mesh. More specifically, but not exclusively, it is related to a surgical stapler having a distal manipulator for positioning a surgical mesh prior to application of the staples.

Chapters 14 and 23, "Lichtenstein Tension-Free Hernioplasty For The Repair of Primary and Recurrent Inguinal Hernias", and "The Transabdominal Preperitoneal Laparoscopic Herniorrhaphy", pages 149-157, and 256-268 of *Nyhus and Condon's Hernia, Fifth Edition*, edited by Robert J. Fitzgibbons and A. Gerson Greenburg, published by Lippincott Williams & Wilkins, Philadelphia, 2002, describe some procedures for repair of inguinal hernias. A sheet of monofilamented polypropylene mesh is mentioned as a material suitable for use in such procedures. After shaping and placement of the mesh in the repair site, it is sutured to adjacent tissue.

While suturing is a long-standing practice for securing the mesh, some stapling is frequently favored because of the speed and relative ease of doing it. At some locations desired for attachment of the mesh to tissue, stapling is possible, but holding and stapling the mesh to tissue at some other locations where attachment is desired, can be challenging, if not impossible, for one pair of hands. Improvement is needed.

SUMMARY

The present invention provides systems and techniques for applying surgical staples and for using staples to hold a surgical mesh, for example during an inguinal hernia repair. The systems and techniques may also be applied during ventral/incisional hernia repair, used for skin closure or used in other surgical procedures as would occur to the skilled artisan. While the actual nature of the invention covered herein can only be determined with reference to the claims appended hereto, certain aspects of the invention that are characteristic of the embodiments disclosed herein are described briefly as follows.

According to one aspect, an improved surgical stapler for attaching surgical mesh includes an elongated shaft having a handle at its proximal end and a downwardly disposed staple discharge port at its distal end. The handle includes a trigger that is configured to cause a supply of staples to be selectively discharged from the discharge port. One or more mesh manipulators are provided near the discharge port and are operable to assist in the positioning of the surgical mesh prior to firing a staple to secure the mesh to tissue. The mesh manipulators may be fixed in position or made to be retractable. In one particular aspect, the mesh manipulator is in the form of an elongated shaft that is selectively extended from a housing mounted beneath the elongated shaft. In another particular aspect, the mesh manipulator comprises a plurality of prongs mounted on oppositely disposed sides of the discharge port.

According to another aspect, a novel surgical stapler comprises an elongated shaft having a handle at its proximal end, a downwardly disposed discharge head at its distal end, and an angled magazine of staples mounted between the discharge head and the shaft. A staple former in the discharge head is driven by a trigger in the handle via an actuating member extending through the shaft. The actuating member may comprise a rigid rod in a straight section of the shaft and a flexible member spanning a curved section of the shaft.

These and other aspects are discussed below.

DETAILED DESCRIPTION OF THE ILLUSTRATED EMBODIMENTS

Figure 1:
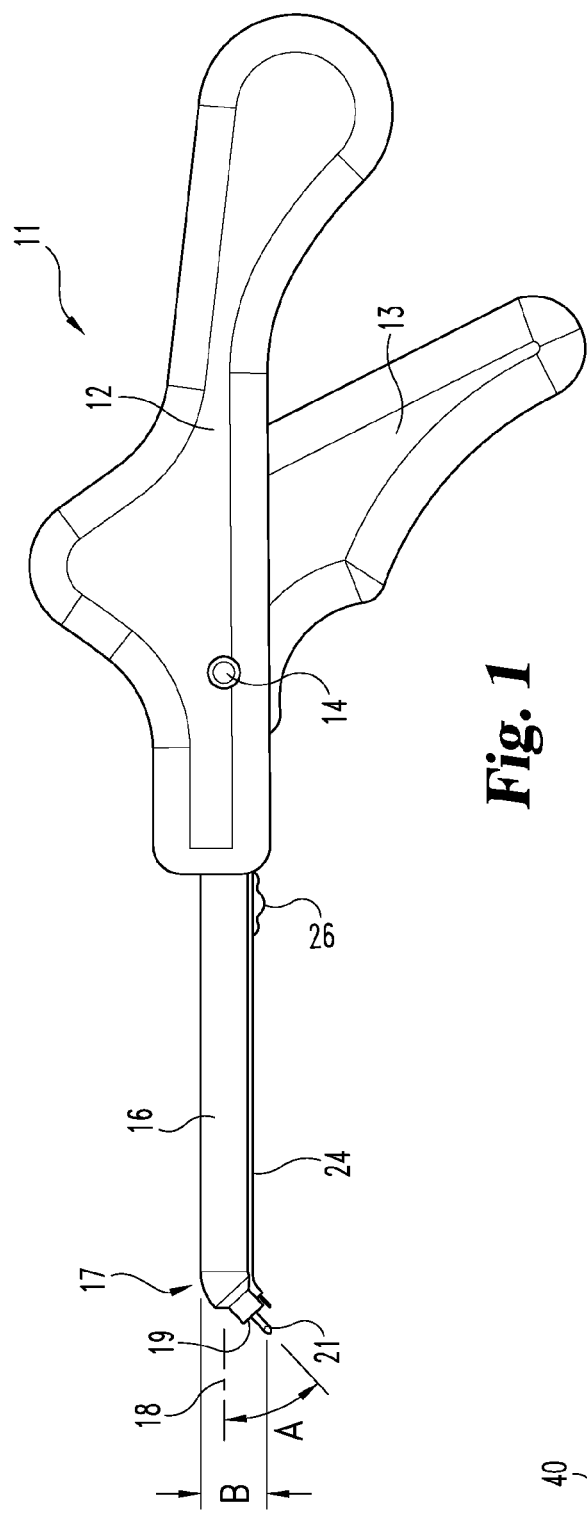
FIG. 1 is a side elevational view of an embodiment of the present invention.
Figure 1A:
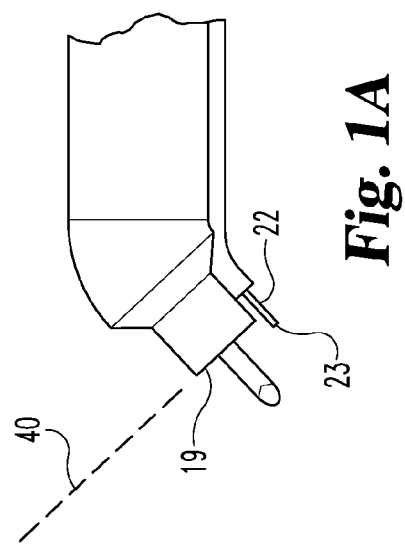
FIG. 1A is an enlarged fragmentary view of a portion of the stapler head showing a staple projecting from the staple exit port and showing the tip of a mesh positioning probe wire.
Figures 2, 2A:
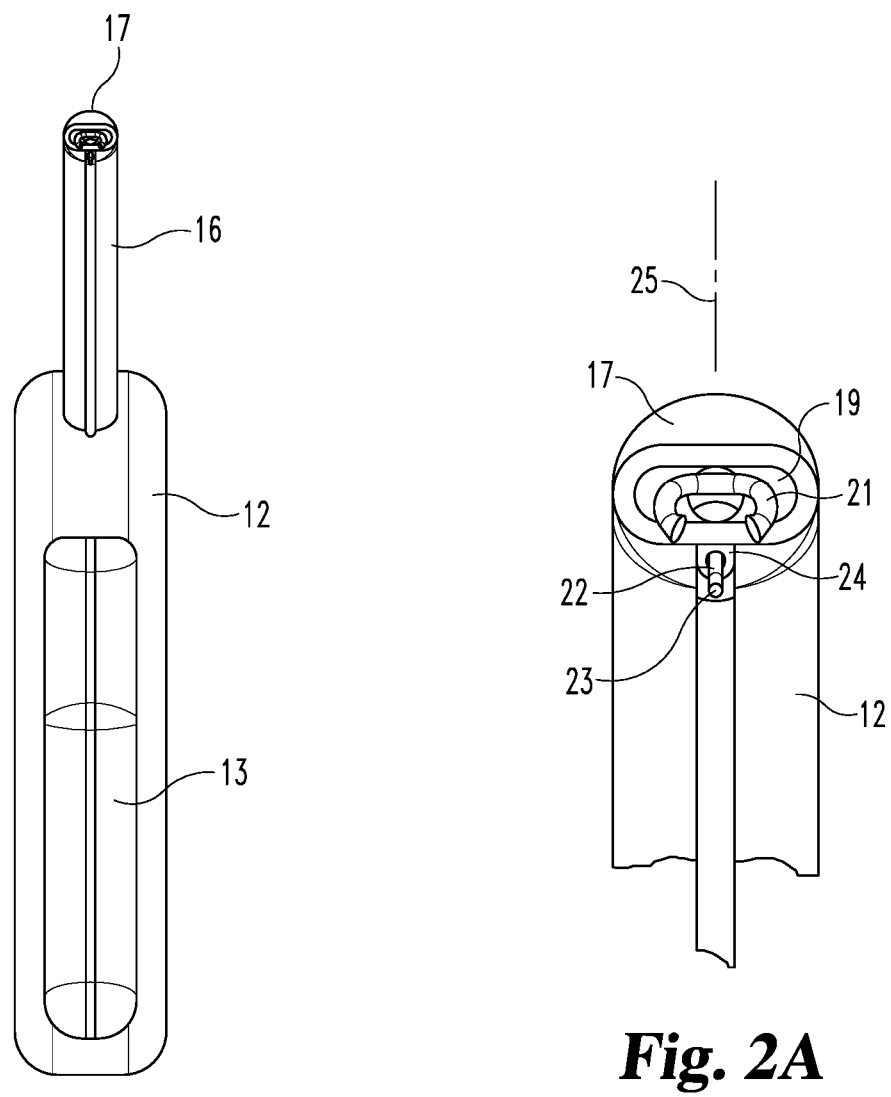
FIG. 2 is a front elevational view of the stapler.
FIG. 2A is an enlarged fragmentary front view of the stapler head portion.

Referring to FIGS. 1-2A, a stapler 11 has a handle 12 with a trigger 13 pivotally mounted to the handle at 14. A tube 16 is fixed to the handle and has a stapler head portion 17 at its distal end. The head portion turns downward at an angle of about forty degrees (A in FIG. 1) from the axis 18 and has a staple discharge port 19 through which staples are shot, one staple for each trigger pull. The trigger coupling to the staple shooter is a two-stage system whereby the staple 21 can be advanced from within the head to a position shown in FIGS. 1 and 1A. Then, upon further pull of the trigger it can be shot through the mesh into the tissue.

One inventive feature is the provision of a mesh manipulator near the outlet port of the stapler. As used herein, a "mesh manipulator" does not include the staple itself, but rather it is a structure other than the staple that is operable to be used to manipulate surgical mesh. In FIGS. 1 and 1A, the mesh manipulator comprises an elongated member or wire 22 having a distal portion including a tip 23 which projects downward under the head 17 in the plane 25 (FIG. 2A) containing the axis 18 of the tube 16 and bisecting the handle 12. This elongated member extends from the tip portion backward through a channel 24 at the bottom of the tube 16. A wire control button 26 slidable on the channel and connected to the proximal end of the wire, is provided to slide the wire forward to extend the tip 23 farther below the staple outlet port 19, or retract it into the channel 24 when, and to what extent desired by the surgeon. Other locations for the wire control knob or button can be used when and desired by the user. One example is in the handle itself.

For purposes of useful mesh manipulation, the wire 22 would often, but not always, be positioned such that the tip 23 projects several millimeters beyond the plane 40 defined by the outlet port 19, as shown in FIG. 1A. For example, it is expected that useful mesh manipulation can be achieved when the tip 23 is at least about 2 mm, 3 mm, 4 mm, 5 mm, 6 mm, 7 mm, 8 mm, 9 mm, or 10 mm distal to plane 40.

Figure 3:
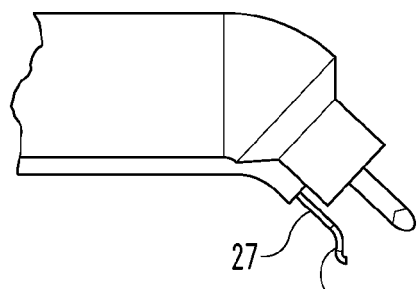
FIG. 3 is an enlarged fragmentary schematic view of the stapler head portion with a probe wire type curved forward to push mesh to a desired position on body tissue for stapling.
Figure 3A:
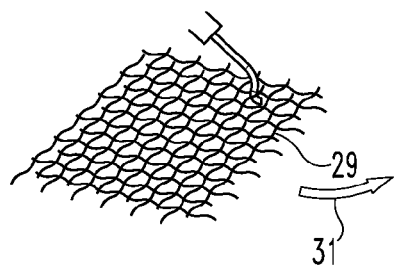
FIG. 3A illustrates the actual use of the wire pushing a piece of mesh forward.

Referring now to FIGS. 3 and 3A, a wire 27 is provided with a curved tip portion 28 curved downward and forward for insertion through the mesh 29 and pushing it forward in the direction of arrow 31 to move it to the position desired for stapling. This forward movement may be made by moving the stapler itself using the handle or by moving the wire by moving the slider button 26.

Figure 4:
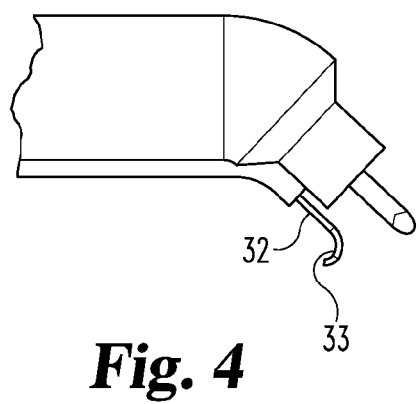
FIG. 4 is a view similar to FIG. 3 but showing the probe wire tip portion angled backward to pull the mesh.
Figure 4A:
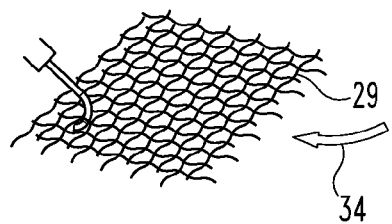
FIG. 4A is similar to FIG. 3A but showing the tip of FIG. 4 engaged to pull the mesh.

Referring to FIGS. 4 and 4A, the wire 32 has a tip portion 33 which is curved rearward to enable the wire tip to pass through the mesh 29 and pull it rearward in the direction of arrow 34 to position the mesh where desired relative to the location at which the stapling through the mesh to the tissue is desired.

Figure 5:
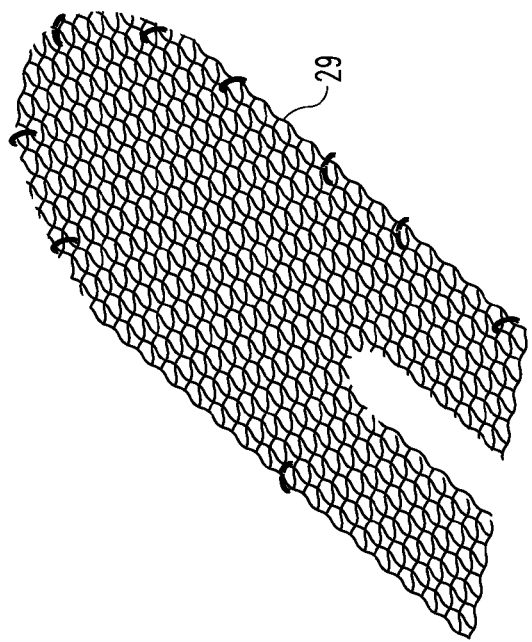
FIG. 5 is a schematic view of a piece of mesh shaped for placement in the repair site and illustrating the location where stapling is desired.

Referring now to FIG. 5, there is a schematic showing the mesh 29 cut from a sheet into a shape desired for placement at the surgery site. There are shown eleven sites at the edges of the mesh indicating where stapling inboard from the edges is desired. This is an example, as different sizes and shapes and numbers of staples may be chosen depending upon the requirements of the site.

Figure 6:
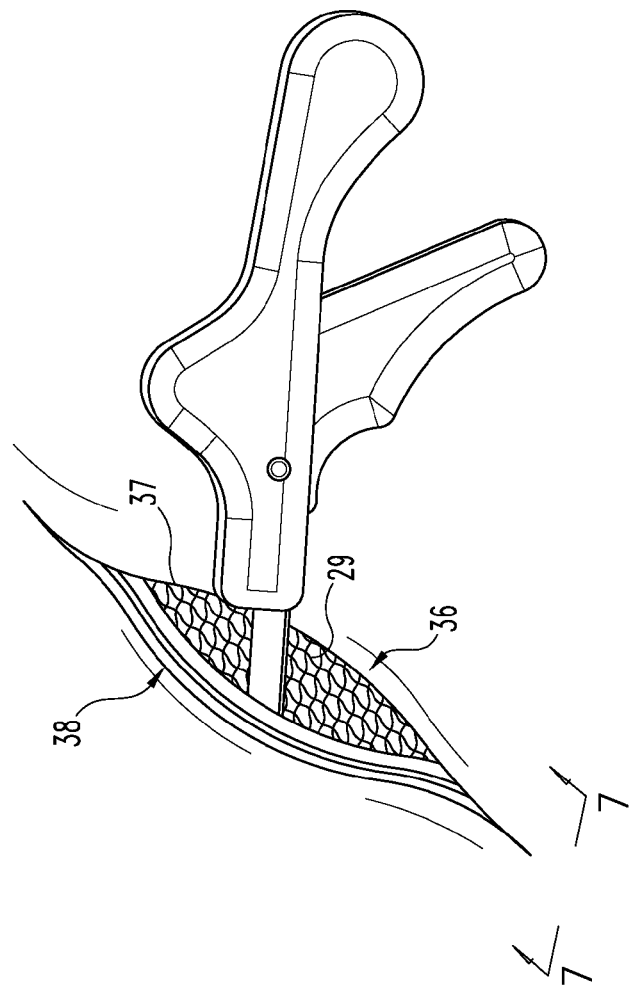
FIG. 6 is a schematic view of the repair site with stapler head in the opening.
Figure 7:
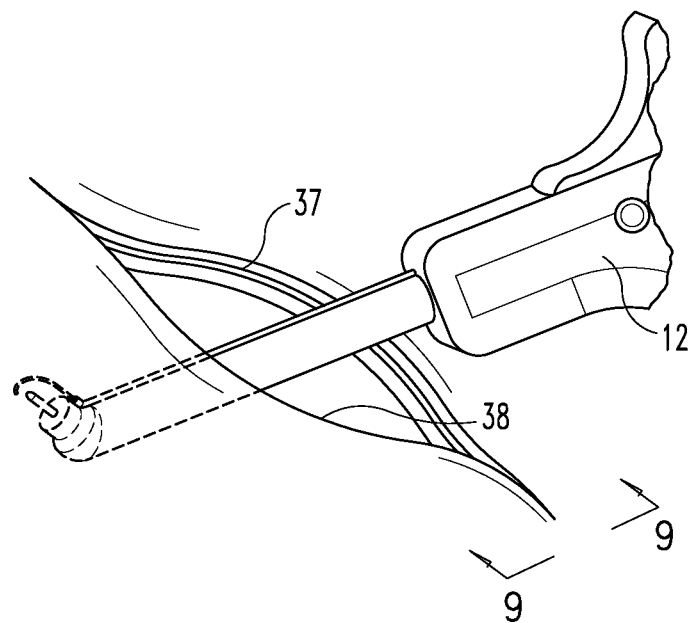
FIG. 7 is a schematic view of the repair site with the stapler in position for stapling the mesh to the underside of body tissue at the far side of the opening.
Figure 8A:
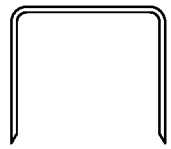
FIG. 8A is a view of a staple before installation.
Figure 8B:
FIGS. 8B, 8C, 8D and 8E represent four possible different configurations of the staple after stapling, the shapes being determined by staple forming features specified for incorporation in the stapler head.
Figure 8C:
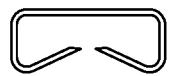
Figure 8D:
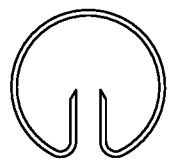
Figure 8E:
Figure 9:
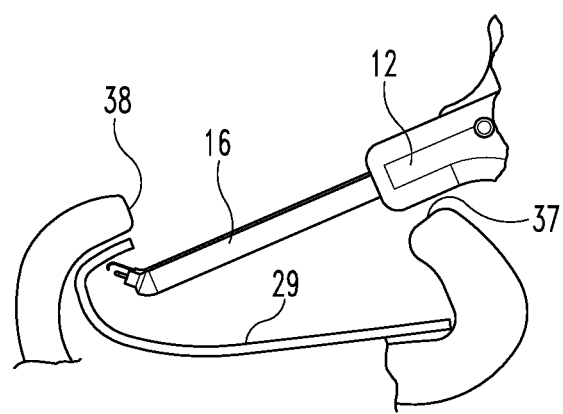
FIG. 9 is a schematic of the site and viewed in the direction of arrows 9-9 in FIG. 7.

FIG. 6 is a schematic illustration of the site with the staple head inserted into the opening 36. Consider that the opening edge 37 nearest the surgeon is referred to in this context, as the near edge, and the opposite edge 38 is the far edge. Attachment of the mesh to tissue below the near edge 37 by stapling can be relatively straight forward with the stapler oriented as shown in FIG. 6, but pulled outward to place the head at the near edge 37 and move the head downward to the mesh and shoot the staple down into the mesh with the prongs into the tissue below. On the opposite edge, the mesh is to be stapled to the upper inside face of the tissue. That is extremely difficult with conventional instruments. But the present invention is capable of being turned upside down as shown in FIGS. 7 and 9 so that the discharge port 19 and wire 23 are facing upwardly to the tissue and pushed or pulled by a wire tip such as shown in FIG. 3 or FIG. 4, depending upon the most effective approach to push or pull the mesh to the location desired for stapling and then fire the staple upward with the prongs through the mesh and into inverted or lofted tissue.

In FIG. 1, for example and without limitation, the head 17 has the discharge port angled down as shown at A. As an example, this angle can be between 30 and 50 degrees from the center line 18 of the shaft. 45 degrees might be optimal.

Figure 10:
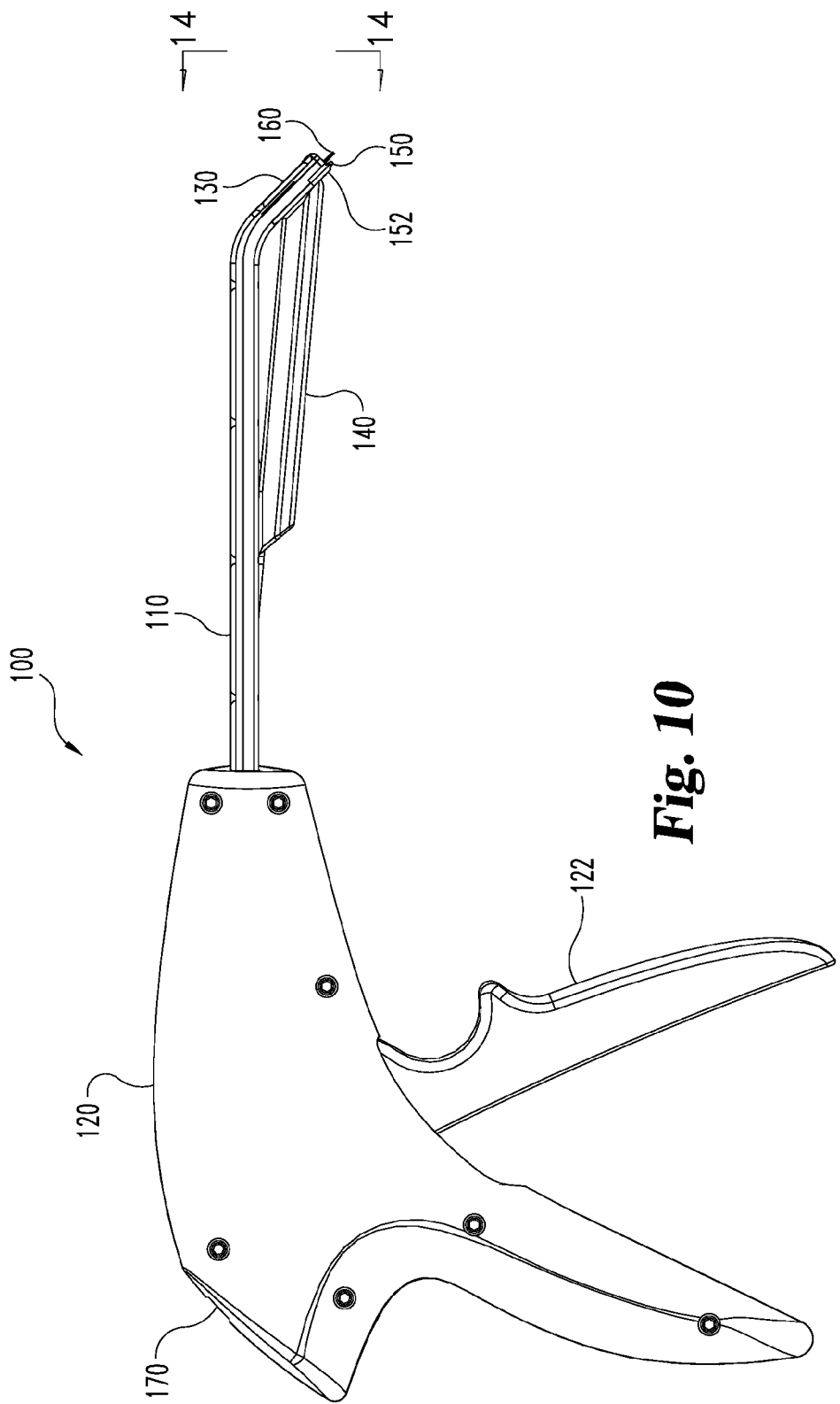
FIG. 10 is a side elevational view of a stapler of new construction.
Figure 11:
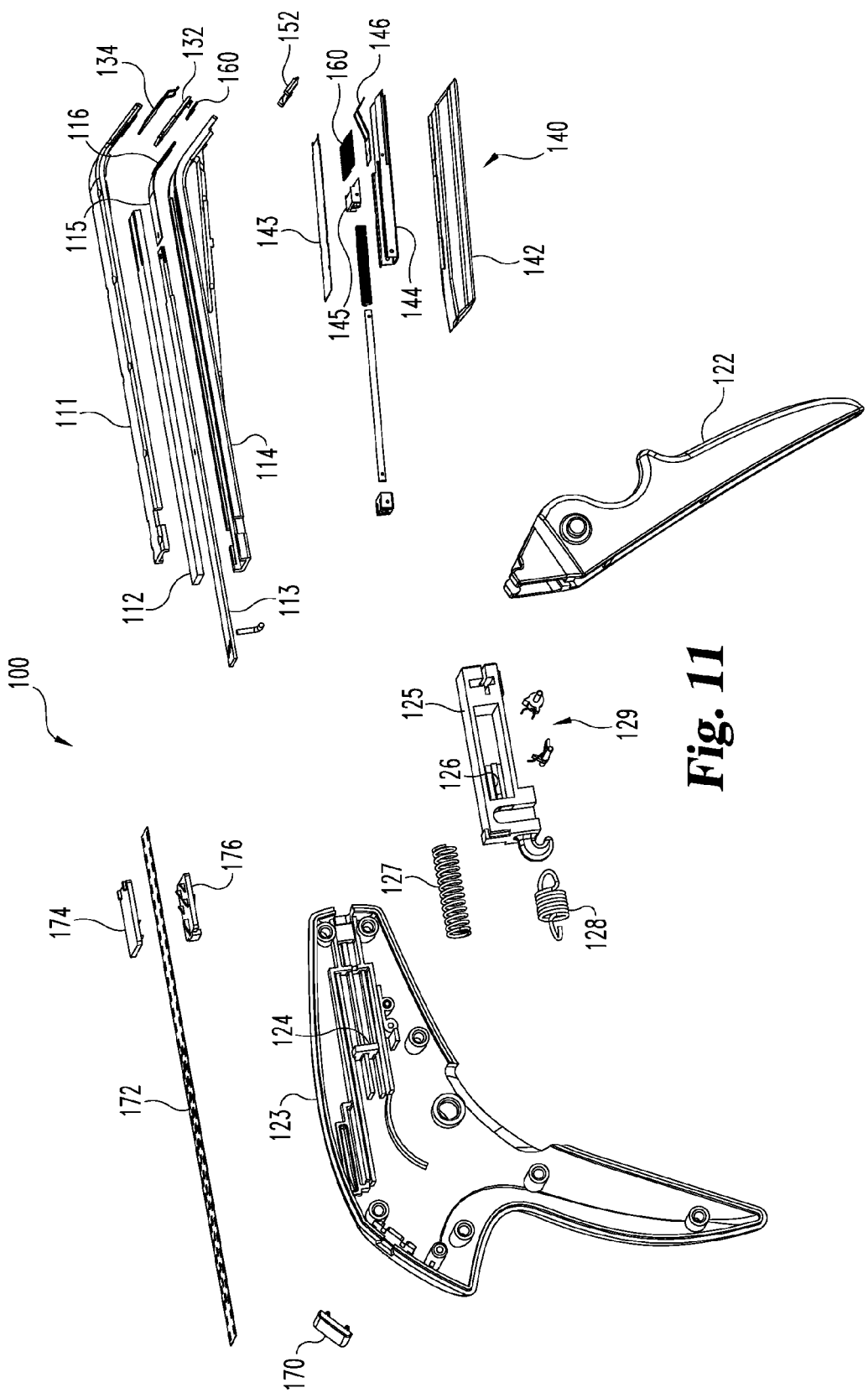
FIG. 11 is an exploded view of the FIG. 10 stapler with the second half of the handle omitted for clarity.

The total offset B between the bottom of the head and top of the shaft is preferably between 12 and 25 millimeters. Other angles and offset dimensions may be used if desired or necessary to the particular surgical site. The overall length between the head and the proximal end of shaft 16 at its entrance to the handle 12 may be 85 millimeters, for example. Again, other dimensions may be determined according to the preference of the surgeon and the nature of the surgical site. The same is true as to the shape and nature of the handle, one example of a different shape is illustrated in FIGS. 10-11 as will be described. The width of the staple between the prongs may be 5 millimeters, for example, but staples of other widths might be selected for particular cases. For example, it may be desirable to produce a fully formed box staple using 0.5 mm staple wire wherein the formed staple has a width of about 7.5 mm and a height of about 3.5 mm. In some tools, it might be considered desirable to make the shaft rotatable in the handle and/or to provide an articulation joint in the shaft near where it enters the handle, but, for the present, it appears that simply inverting the handle from the attitude as shown in FIG. 1 to that as shown in FIGS. 7 and 9 would appear to be adequate. A variety of mechanisms for discharging a staple can be implemented. For example, U.S. Pat. No. 5,829,662 and U.S. Pat. No. 5,743,456 describe endoscopic stapling equipment that could be adapted to implement the present invention.

Referring now to FIGS. 10-14A, stapler 100 comprises a handle unit 120 and a downwardly disposed discharge head 130 at either end of an elongated shaft 110. A staple magazine 140 containing a supply of staples (e.g. 15) is mounted to the underside of the shaft 110. Trigger 122 is operative to cause a staple 160 to be formed and discharged from the outlet port 162 of head 130. Successive pulls of the trigger form and discharge successive staples from the magazine 140, and a running staple count is displayed in a window at 170.

Formation and discharge of a staple is accomplished via a single stroke of pusher plate 116, which is coupled to trigger 122 via a mechanical linkage that extends through the shaft 130. More specifically, drive block 125 is mounted in a slot in housing 123 with one end of compression spring 127 over tab 126 and the other end against tab 124. The drive block 125 is coupled to a driver 113 or rigid bar, which is slidably disposed in the channel of shaft 110 defined between the upper cover 111 and base 114. A stiffener 112 is also provided in the shaft channel to increase structural rigidity of the elongated straight portion of the shaft 110. A flexible pusher 115 is coupled to the end of driver 113 and traverses the curved portion of channel, which includes support ribs for flexible pusher 115 in the upper cover 111 to reduce the possibility that the flexible pusher 115 would buckle or otherwise deform. Pusher plate 116 is laminated to the distal end of flexible pusher 115 for a seamless connection. Other connections are possible as well.

In operation, squeezing the trigger 122 drives block 125 to the right (FIGS. 10, 11), overcoming the restoring forces of springs 127, 128. Springs 127 and 128 each function as a return spring, thereby providing redundancy, but their spring parameters may be selected to produce a desired effect (e.g. substantially increased return force at max trigger depression). As block 125 travels right, a one way clutch assembly 129 engages cogs (not shown) on the underside of block 125 to prevent retraction of block 125 short of a full stroke. In addition, shuttle plate 176 is carried above block 125 and operates to advance numbered ribbon 172, which is sandwiched between shuttle plate 176 and stay plate 174 and provides a running count of staples via a window adjacent backing plate 170.

Figure 12:
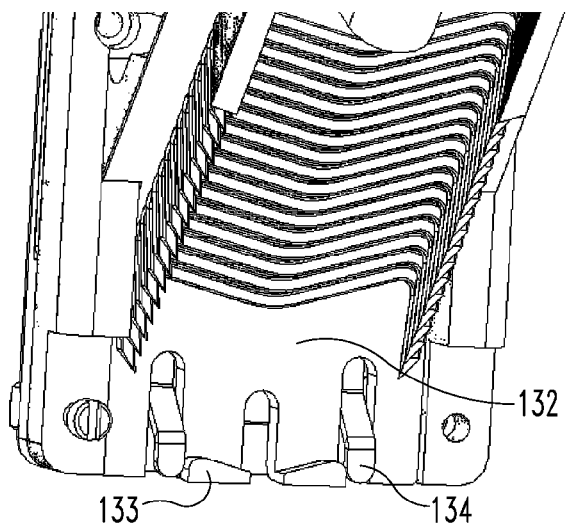
FIG. 12 is an underside view of the staple discharge head of the FIG. 10 stapler with the front wall piece 152 and the supporting magazine 140 for the staples removed for clarity.
Figure 13:
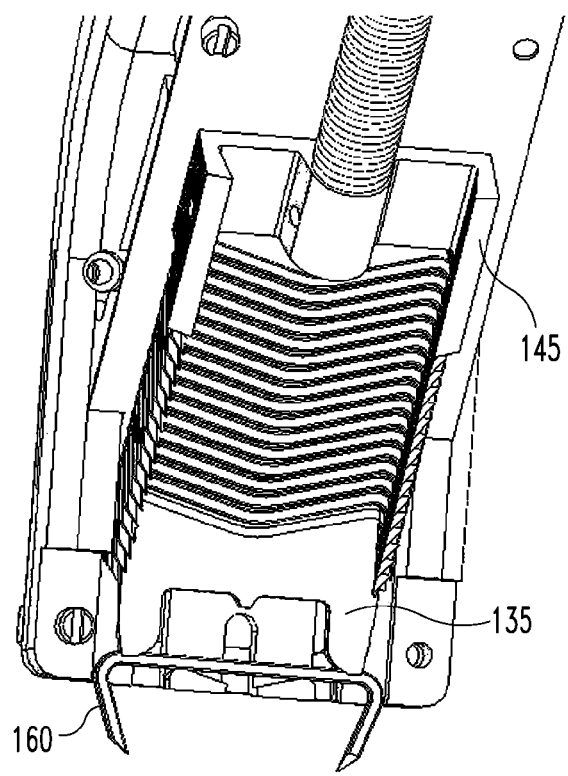
FIG. 13 is the underside view of FIG. 13 with a staple partially formed.

At the beginning of a stoke, pusher plate 116 is withdrawn into the discharge head 130, and the first staple in the magazine 140 is advanced into the firing breech. As shown in FIGS. 12 and 13, the staples in the magazine 140 are in the form of an angled stack, with each staple 160 in the stack oriented in its firing direction (i.e. parallel to the back wall 132 of the breech) and the axis of the stack 40-50° from orthogonal to the firing direction.

As illustrated, the staples in the magazine are generally "M" shaped and are mounted over the front rails of a holder 144, with each hump over one of the rails. A cover plate 143 is secured to the top of holder 144 and a spring pusher 145 biases the staple stack 160 towards the open, angled end of the holder 144. As illustrated, the spring biasing pusher 145 has an uncompressed length greater than the length of the staple stack, which can serve to provide a more constant force on the staple stack as staples are discharged. Guide 146 is positioned at the open end of holder 144 and provides angled fingers that prevent the staples from dropping out the angled, open end prematurely. The staple magazine 140 is mounted to supporting rails on base 114 and covered by a protective shroud 142, and front wall piece 152 is secured to complete the assembly.

As it advances in its stroke, the forming fingers 135 of pusher plate 116 pick off the first staple from the stack and form the staple around anvil 133. FIG. 13 illustrates a partially formed staple extending from outlet port 162. Continuation of the forming fingers 135 serves to fully form the staple into a desired box like shape, and preferably with the staple prongs inverted slightly rearward. Retraction of forming fingers 135 releases the leaf springs 134, which had been displaced on the downstroke, which serves to displace the now-formed staple from anvil 133. Because the formed staple is narrower, it slips readily through the wider central opening of outlet port 162, as shown in FIGS. 14A-D.

Figure 14A:
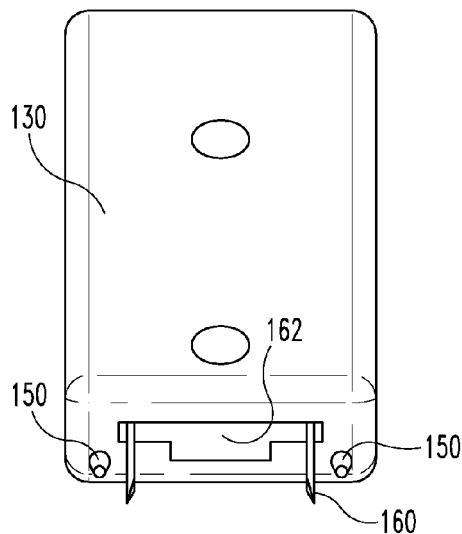
FIG. 14A is an end view of the discharge head of the FIG. 10 stapler, viewed in the direction of arrows 14-14 in FIG. 10.
Figure 14B:
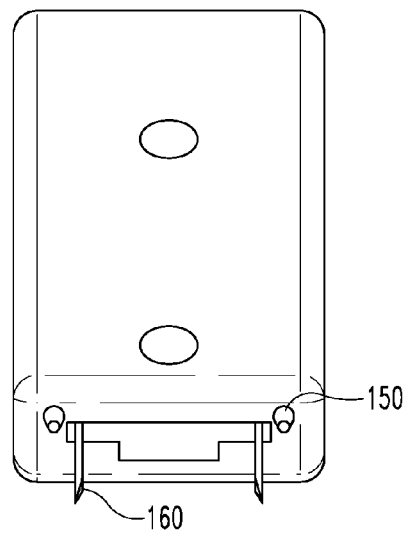
FIGS. 14B-D are views of alternative arrangements for the prongs on the discharge head.
Figure 14C:
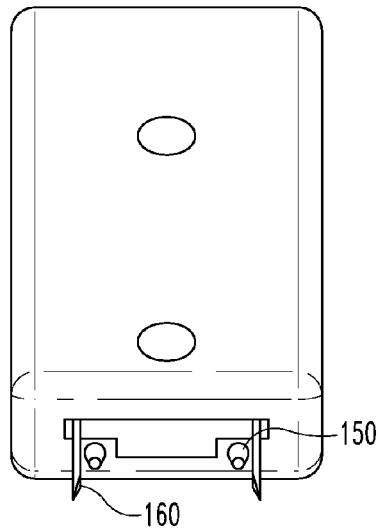
Figure 14D:
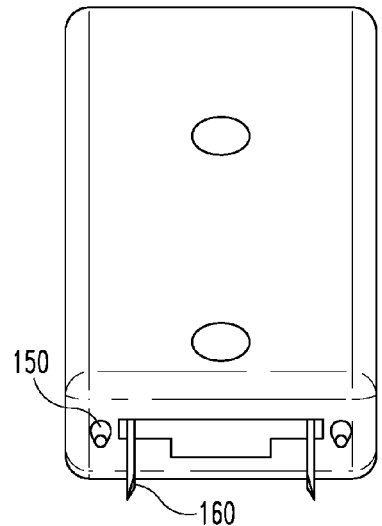

As illustrated, stapler 100 includes fixed prongs 150 on the underside outside of outlet port 162. Prongs 150 serve as mesh manipulators and may be used in any fashion contemplated herein. FIGS. 14B-D provide illustrations of additional or alternative locations for mesh manipulating prongs about the staple discharge port. Fixed prongs can also be used in combination with a retractable wire to provide further combinations of manipulating capabilities.

It is also contemplated that stapler 100 can be used without any means for mesh manipulation.

Numerous variations of the staplers described herein can be employed. For example, it may be desirable to provide one or more points of articulation along the shaft of the staplers described. As one example, a joint capable of 90° articulation can be along shaft 110, for example near where shaft 110 and handle 120 meet. The provision of such an articulation joint may make it easier for the right handed surgeon, when operating on a right inguinal hernia, to place the staples that attach the mesh to the inguinal ligament.

Staples used herein can be absorbable or non absorbable with material inside the absorbable material for forming the staple. Square shaped, round shaped, G shaped, etc. The staples can be stacked together along a rack inside the shaft that guides the staples to the distal end of the shaft with a spring loaded action, or a mechanism in the handle.

Procedures

Either under local anesthesia with sedation or general anesthesia, the lower abdomen is prepped and draped. A linear 6 to 8 cm. skin incision is made along the natural skin lines. Hemostasis is obtained. The external oblique aponeurosis is divided, exposing the spermatic cord. Depending on what type of hernia, the hernia sac is dissected from adjacent tissues, emptied of any contents and pushed back into the peritoneal cavity. The mesh to be used, is cut to its standard shape and size, and a tail slit is placed to accommodate the spermatic cord. The stapler is then used to fix the mesh to the insertion of the rectus sheath and along the inguinal ligament. More specifically, the stapler is used to fix the mesh to the rectus sheath, above its insertion to the pubic bone. (The stapler is sized and shaped to assure the safety of the femoral vessels and nerve.) The upper edge of the mesh is stapled to the rectus sheath and the internal oblique apponeurosis avoiding the iliohypogastric nerve. Either a staple or a single non-absorbable suture is then placed through the lower edges of the tails at the level of the internal ring. The wound is then closed in layers after all bleeding has been stopped and the sponge and instrument count is correct. The wound (i.e. the skin) can be closed with the stapler or with a conventional suture.

It is to be appreciated that what has been described includes an improved surgical stapler for attaching surgical mesh, comprising an elongated shaft having a handle at its proximal end and a downwardly disposed staple discharge port at its distal end, wherein the handle is operable to cause a supply of staples to be selectively discharged from the port; and one or more mesh manipulators near the port and projecting distal to the plane defined by the port.

What has also been described includes an apparatus for use by a person stapling mesh to body tissue at a site of inguinal hernia surgery and comprising: a handle for holding the apparatus adjacent the surgery site, and having a proximal end and a distal end; a shaft defining a longitudinal axis and having a proximal end and a distal end and having the proximal end mounted to the distal end of the handle; a staple discharge head having one end with a mounting portion connected to the distal end of the shaft, and having another end with a staple exit port; the head adapted to fire a staple out from said head through said port along a line and in a direction away from the handle, wherein the direction of staple firing is downward relative to the longitudinal axis of the shaft; an elongated member mounted to said shaft and extending generally parallel to the shaft and in a direction forward away from said handle, the member having a distal end portion in a plane containing the direction of staple firing, and the distal end portion of said member being spaced from said line and under the line; and the distal end portion of said member having a tip configured to engage a mesh useful for embedding in a body cavity during inguinal hernia surgery, for connecting and moving said mesh to a location for stapling the mesh to body tissue at the surgery site. In one refinement, the distal end portion of said member is strait and curves downward and then forward in said plane to said tip. In another refinement, the distal end portion of said member is strait and curves downward and then rearward in the plane to the tip. In another refinement, a guide on the shaft receives the elongated member and has a proximal end near the handle and a distal end opening exposing the distal end portion of the wire forward of the distal end opening of said guide, and confining the elongated member from the distal end portion of the member rearward to a location adjacent the handle. It may further include a manipulator on the elongated member adjacent the handle for alternately advancing and retracting the tip of the member.

What is also described is an apparatus for use in stapling mesh to body tissue at a site of inguinal hernia repair surgery and comprising: a shaft having a proximal end and a distal end; a staple discharging head at the distal end of the shaft; a staple inside the head, the staple having a generally U-shaped configuration with spaced prongs in a first plane; and a discharge port on the head for discharge of said staple outward from said head through the discharge port; and a mesh manipulator connected to the head and having a tip adjacent the port the tip of the manipulator is spaced from said first plane a short distance from said first plane to avoid contact by the staple when discharged outward from the port into the mesh.

What is also described includes, during inguinal hernia repair, a method of attaching a mesh covering herniated membrane, to body tissue adjacent and bordering the site of the herniation, and comprising: inserting the head of a stapling apparatus into an opening bordered by said tissue and directing a staple discharge port downward toward said mesh at a near side of said opening and firing staples from said port through said mesh into some of said tissue adjacent said herniation, at multiple locations on the near side of said opening; moving the head of a stapling apparatus in an opening bordered by said tissue and directing a staple discharge port upward toward said mesh at a far side of said opening and firing staples from said port through said mesh into some of said tissue, at multiple locations on the far side of said opening. The method may further include engaging said mesh with a probe point mounted to said head and located between said port and said mesh, and moving said mesh with said probe to position said mesh at a location on said tissue where a staple is to be fired into said mesh and said tissue. The method may further include moving said mesh is by pushing said mesh with said probe point and/or pulling said mesh with said probe point. Pulling the mesh may be used to lift said mesh on said far side. The mesh may be pierced to facilitate said moving of said mesh.

What is claimed is:

1. A surgical stapler for use during an open hernia repair, comprising:
   an elongated shaft having a handle at its proximal end and a staple discharge head at its distal end, a longitudinal axis of the staple discharge head forming an angle between 30 degrees and 50 degrees relative to the longitudinal axis of the elongated shaft, the staple discharge head defining a staple discharge port, wherein the handle is operable to cause a supply of staples to be selectively discharged from the port;
   one or more mesh manipulators positioned on the staple discharge head adjacent the staple discharge port, the mesh manipulators configured to penetrate into a surgical mesh to move the surgical mesh to a desired position for stapling; and
   a staple magazine mounted to the discharge head and to the elongated shaft, wherein a longitudinal axis of the staple magazine is oriented between 40 degrees and 50 degrees relative to the longitudinal axis of the elongated shaft during the open hernia repair.

2. The stapler of claim 1 wherein the one or more mesh manipulators comprise one or more fixed prongs.

3. The stapler of claim 2 wherein a plurality of fixed prongs are disposed on opposing sides of the discharge port.

4. The stapler of claim 2 wherein the one or more mesh manipulators comprise a wire having a non-linear portion.

5. The stapler of claim 1 wherein the one or more mesh manipulators are retractable.

6. The stapler of claim 1 wherein a staple former in the discharge head is driven by a trigger in the handle via an actuating assembly extending through the shaft.

7. The stapler of claim 6 wherein the actuating assembly comprises a rigid rod in a straight section of the shaft and a flexible member spanning a curved section of the shaft.

8. A surgical stapler comprising:
   an elongated shaft having a handle at its proximal end, a discharge head at its distal end wherein a longitudinal axis of the discharge head is disposed at an angle between 30 degrees and 50 degrees relative to the longitudinal axis of the elongated shaft, the shaft having a middle portion that spans between the proximal end and the distal end;
   a magazine of staples mounted between the discharge head and the middle portion of the shaft, a longitudinal axis of the magazine of staples disposed at an angle between 40 degrees and 50 degrees relative to the longitudinal axis of the elongated shaft, the magazine of staples positioned exteriorly to the shaft; and
   a pusher plate positioned in the discharge head, the pusher plate is configured to move forward in the discharge head to remove a single staple from the magazine of staples.

9. The surgical stapler of claim 8 wherein the discharge head is driven by a trigger in the handle via an actuating assembly extending longitudinally through the shaft.

10. The surgical stapler of claim 9 wherein the actuating assembly comprises a rigid rod in a straight section of the shaft and a flexible member spanning a curved section of the shaft, and the pusher plate is attached to the flexible member.

11. The surgical stapler of claim 8 further comprising one or more mesh manipulators extending under the discharge head.

12. The surgical stapler of claim 11 wherein the one or more mesh manipulators comprise a plurality of fixed prongs.

13. The surgical stapler of claim 11 wherein the one or more mesh manipulators are retractable.

14. An apparatus for use by a person stapling mesh to body tissue at a site of inguinal hernia surgery, comprising:
   a handle for holding the apparatus adjacent the surgery site, and having a proximal end and a distal end;
   a rigid shaft having a proximal end and a distal end and a longitudinal axis that spans between the proximal end and the distal end, and the shaft having the proximal end mounted to the distal end of the handle;
   a staple discharge head having one end with a mounting portion connected to the distal end of the shaft, and having another end with a staple exit port, a longitudinal axis that spans between the ends of the staple discharge head forming an acute angle relative to the longitudinal axis of the shaft;
   the head adapted to fire a staple out from the head through the port along a line and in a direction away from the handle, wherein the direction of staple firing is at an acute angle relative to the longitudinal axis of the shaft;
   a plurality of mesh manipulating prongs extending under the staple discharge head in a direction parallel to the longitudinal axis of the staple discharge head, wherein said prongs each include a distal portion having a tip to penetrate into a mesh positioned in a body cavity during inguinal hernia surgery, the mesh manipulating prongs configured to move said mesh to a location for stapling the mesh to body tissue at the surgery site; and
   a staple magazine having a length that spans between the staple exit port of the discharge head and the rigid shaft, wherein a longitudinal axis of the staple magazine is oriented at an acute angle relative to the longitudinal axis of the rigid shaft during the open hernia repair.

15. The apparatus of claim 14 wherein the prongs extend at least about 3 mm distal to a plane defined by a staple outlet port in the head.

16. The surgical stapler of claim 10 wherein the pusher plate includes a forming finger to remove the single staple from the magazine of staples.

17. The surgical stapler of claim 8 further comprising a stiffener provided in the elongated shaft to increase rigidity of the shaft.

18. The apparatus of claim 14 wherein the longitudinal axis of the staple discharge head forming the acute angle relative to the longitudinal axis of the shaft is between 30 degrees and 50 degrees.

* * * * *